United States Patent
Wieczorek et al.

(10) Patent No.: US 10,989,819 B2
(45) Date of Patent: Apr. 27, 2021

(54) GAMMA RADIATION DETECTOR WITH PARALLAX COMPENSATION

(71) Applicant: KONINKLIJKE PHILIPS N.V., Eindhoven (NL)

(72) Inventors: Herfried Karl Wieczorek, Aachen (DE); Torsten Solf, Aachen (DE); Thomas Frach, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 73 days.

(21) Appl. No.: 16/340,178

(22) PCT Filed: Oct. 24, 2017

(86) PCT No.: PCT/EP2017/077100
§ 371 (c)(1),
(2) Date: Apr. 17, 2019

(87) PCT Pub. No.: WO2018/077840
PCT Pub. Date: May 3, 2018

(65) Prior Publication Data
US 2020/0284922 A1 Sep. 10, 2020

(30) Foreign Application Priority Data
Oct. 28, 2016 (EP) .................................... 16196204

(51) Int. Cl.
*G01T 1/20* (2006.01)
*G01T 1/164* (2006.01)
*A61B 6/03* (2006.01)

(52) U.S. Cl.
CPC ............ *G01T 1/2018* (2013.01); *A61B 6/037* (2013.01); *G01T 1/1644* (2013.01)

(58) Field of Classification Search
CPC ...... A61B 6/037; G01T 1/1644; G01T 1/2018
See application file for complete search history.

(56) References Cited

U.S. PATENT DOCUMENTS 7,692,156 B1 4/2010 Nagarkar
7,989,771 B2 8/2011 Wieczorek
(Continued)

FOREIGN PATENT DOCUMENTS

WO 2007089962 8/2007

OTHER PUBLICATIONS

Alhassen et al: "Depth-of-Interaction Compensation Using a Focused-Cut Scintillator for a Pinhole Gamma Camera", IEEE Transactions on Nuclear Science, IEEE Service Center, New York, NY, US, vol. 58, No. 3, Jun. 1, 2011.

*Primary Examiner* — Mark R Gaworecki

(57) ABSTRACT

The invention relates to a gamma radiation detector that provides compensation for the parallax effect. The gamma radiation detector includes a plurality of scintillator elements, a planar optical detector array, and a pinhole collimator that includes a pinhole aperture. Each scintillator element has a gamma radiation receiving face and an opposing scintillation light output face. The gamma radiation receiving face of each scintillator element faces the pinhole aperture for generating scintillation light in response to gamma radiation received from the pinhole aperture. The scintillator elements are arranged in groups. Each group has a group axis that is aligned with the pinhole aperture and is perpendicular to the radiation receiving face of each scintillator in that group. The scintillation light output faces of each of the scintillator elements are in optical communication with the planar optical detector array.

22 Claims, 3 Drawing Sheets

(56) References Cited

U.S. PATENT DOCUMENTS

| | | |
|---|---|---|
| 2002/0153492 A1 | 10/2002 | Sekine |
| 2008/0001088 A1* | 1/2008 | Joung .................... A61B 6/037 250/363.1 |
| 2012/0039446 A1* | 2/2012 | Cui ...................... A61B 6/4291 378/149 |
| 2012/0223239 A1 | 9/2012 | Bernhardt |
| 2013/0126744 A1 | 5/2013 | Jansen |
| 2014/0233690 A1 | 8/2014 | Hashimoto |
| 2015/0235723 A1* | 8/2015 | Lee ....................... G01T 1/1648 250/505.1 |
| 2016/0192896 A1 | 7/2016 | Perkins |

* cited by examiner

GAMMA RADIATION DETECTOR WITH PARALLAX COMPENSATION

CROSS REFERENCE TO RELATED APPLICATIONS

This application is the U.S. National Phase application under 35 U.S.C. § 371 of International Application No. PCT/EP2017/077100, filed Oct. 24, 2017, published as WO 2018/077840 on May 3, 2018, which claims the benefit of European Patent Application Number 16196204.8 filed Oct. 28, 2016. These applications are hereby incorporated by reference herein.

FIELD OF THE INVENTION

The invention relates to scintillation-type gamma detector. More specifically the gamma detector provides compensation for parallax effects. The gamma detector finds application in gamma detectors in general. However, it finds particular application in a gamma imaging system such as a Single Photon Emission Computed Tomography, i.e. SPECT, imaging system in the nuclear medicine field and will be described with reference thereto.

BACKGROUND OF THE INVENTION

In the nuclear medicine field the functioning of various organs is studied by measuring the distribution of a radiotracer in the body. The radiotracer is typically a gamma emitter that is injected into the patient by a physician. The radiotracer has an affinity with various biological molecules and processes which results in the radiotracer being preferentially absorbed in certain regions of interest within the body. After a predetermined uptake time, these regions of interest are monitored or imaged using one or more gamma detectors that detect gamma quanta emitted by the radiotracer during its radioactive decay.

A sub-class of gamma detectors are scintillation-type detectors. In these, a scintillator element generates a light pulse in response to each received gamma quant. Depending on the scintillator material and the energy of the gamma quanta that are to be detected, a scintillator element may be some 3-30 mm in length. An optical detector subsequently detects the light pulse generated within the scintillator element and thereby indicates that a gamma quant has been received. In order to control the directional sensitivity of each gamma detector a collimator is typically disposed on the radiation-receiving side of the scintillator. A collimator for a gamma detector typically takes the form of one or more apertures formed in a dense metal plate of e.g. lead or tungsten. The apertures, or septa, restrict the field of view of the gamma detector by attenuating gamma quanta that originate from outside the field of view. The septa may be some 10-40 mm in length depending on the energy of the gamma quanta. Such a gamma detector that includes a collimator may be arranged to monitor, i.e. determine the total emission from, or indeed to image, a region of interest such as an organ within the body in order to determine a radiotracer distribution as described above.

A sub-class of collimators that find application in a gamma detector are pinhole collimators. In its simplest form a pinhole collimator is defined by a small hole in a gamma-attenuating plate. The size and shape, specifically the aspect ratio, of the hole, together with the distance between hole and detector, can be set in order to provide a tradeoff between spatial resolution and sensitivity. The gamma acceptance angle, i.e. the angle relative to normal incidence on the gamma-attenuating plate, is limited by the aspect ratio of the hole itself, and is determined by the ratio of the width of the hole to its length along the radiation receiving direction. In addition, the gamma acceptance angle can be limited by septa that are arranged to separate the parts of the detector that receive gamma radiation through a specific pinhole from each other. A high aspect ratio of a hole, a wide detector area under each pinhole, or a short distance between pinholes and detector each provide a wide acceptance angle that offers high sensitivity but introduces the problem of parallax.

Parallax in such a gamma detector configuration arises from the statistical nature of absorption of gamma quanta in the scintillator element. Whilst the majority of gamma quanta are absorbed at an absorption depth that is characteristic of the particular scintillator element material, some gamma quanta are absorbed at much shorter depths and some are absorbed at much longer depths. When benefitting from a wide acceptance angle from a pinhole collimator the range of depths over which quanta are absorbed results in a lateral, with respect to the pinhole, distribution in the point at which the gamma quanta are absorbed. This results in a lateral variation, in the scintillator, in the determined origin of the scintillation light pulse and thus an uncertainty in the direction from which the gamma quanta are received. This uncertainty is termed a parallax effect, or a depth of interaction, i.e. DOI, effect. In gamma imaging systems in particular such parallax effects degrade spatial resolution.

Document WO2007089962A1 addresses the above issue of parallax effects by disposing at least one radiation detection head adjacent a field of view to detect radiation from the field of view. The radiation detection head includes a collimator with an opening through which radiation rays emanating from the field of view can pass, and a detection system forming an arcuate surface focused on the collimator opening for detecting radiation so that radiation rays received through the collimator opening strike the arcuate surface substantially perpendicular to an incremental area of the arcuate surface at which the radiation strikes.

A document U.S. Pat. No. 7,692,156 B1 describes radiation detection devices having beam-oriented scintillators. A radiation detection device includes a beam-oriented pixellated scintillator disposed on a substrate, the scintillator having a first pixel having a first pixel axis and a second pixel having a second pixel axis, wherein the first and second axes are at an angle relative to each other, and wherein each axis is substantially parallel to a predetermined beam direction for illuminating the corresponding pixel.

A document by Fares Alhassen et al, entitled "Depth-of-Interaction Compensation Using a Focused-Cut Scintillator for a Pinhole Gamma Camera", IEEE Transactions on nuclear Science, Vol. 58, No. 3, 1 Jun. 2011, describes a preclinical SPECT system. A pixellated, focused-cut (FC) scintillator, with its pixels laser-cut so that they are collinear with incoming rays is disclosed for compensating for parallax errors introduced by a pinhole collimator of the SPECT system.

SUMMARY OF THE INVENTION

The present invention seeks to reduce parallax effects in a gamma detector. Further advantages from the described invention will also be apparent to the skilled person. Thereto a gamma radiation detector, a SPECT imaging system, a gamma imaging camera, a method of image reconstruction and a computer program product are provided.

The gamma radiation detector includes a plurality of scintillator elements, a planar optical detector array, and a pinhole collimator comprising a pinhole aperture. Each scintillator element includes a gamma radiation receiving face and an opposing scintillation light output face. The gamma radiation receiving face of each scintillator element is arranged to face the pinhole aperture in order to generate scintillation light in response to gamma radiation received from the pinhole aperture. The plurality of scintillator elements are arranged in a plurality of groups; each group including one or more scintillator elements and each group having a group axis that is aligned with the pinhole aperture and that is perpendicular to the radiation receiving face of each of the one or more scintillators in each group. Moreover the scintillation light output face of each of the plurality of scintillator elements are in optical communication with the planar optical detector array.

Since each group axis is aligned with the pinhole aperture it is arranged that gamma quanta absorbed within different groups are absorbed along their respective group axis. This reduces the parallax effect by reducing the gamma quanta acceptance angle of each group, as compared to for example orienting scintillator elements with their group axes parallel to one another. By arranging that the radiation receiving faces of each group are perpendicular to, i.e. within +/−5 degrees of exactly perpendicular to, their respective group axis, a more uniform scintillation light distribution pattern is achieved within the scintillator element. Advantageously because the scintillation light output face of each scintillator element is in optical communication with the planar optical detector array a flat optical detector array can be used. This simplifies the manufacturing and assembly of the optical detector array.

In accordance with one aspect of the invention the plurality of groups include a first group and a second group. Moreover the group axis of the second group is tilted at a tilt angle with respect to the group axis of the first group. The scintillation light output face of each of the one or more scintillator elements in the second group is also tilted at the tilt angle with respect to its corresponding gamma radiation receiving face such that the scintillation light output face of each of the one or more scintillator elements in the second group is parallel to, i.e. within +/−5 degrees of exactly parallel to, the scintillation light output face of each of the one or more scintillator elements in the first group. Advantageously the parallel arrangements of the scintillation light output faces provides a robust means of coupling the scintillator elements to the planar optical detector array. Moreover high light coupling efficiency can be achieved with the array.

In accordance with another aspect of the invention the plurality of groups include a first group and a second group. The group axis of the second group is tilted at a tilt angle with respect to the group axis of the first group. Moreover the scintillation light output face of each scintillator element in the second group is parallel to its corresponding gamma radiation receiving face. Furthermore the second group includes one or more wedge-shaped light guides disposed between each scintillator element of the second group and the planar optical detector array. Each wedge-shaped light guide has a first face and a second face. The second face is arranged at the tilt angle to the corresponding first face in order to couple scintillation light between the scintillation light output face of the corresponding scintillator element and the planar optical detector array via the first face and the second face. Advantageously the parallel arrangement of each scintillator element's gamma radiation receiving face with respect to its scintillation light output face in combination with the wedge shaped light guide provides high light coupling efficiency with the array. Moreover it permits the use of simpler manufacturing methods in making the scintillator elements. Such scintillator shapes are more robust to handling during assembly.

In accordance with another aspect of the invention a SPECT imaging system includes the inventive gamma radiation detector. Advantageously the SPECT imaging system generates images with improved resolution as a result of including the inventive gamma radiation detector.

In accordance with another aspect of the invention a method of image reconstruction includes i) receiving, from the planar optical detector array of the inventive gamma radiation detector, gamma decay event data corresponding to a number of scintillation light pulses detected by a portion of the planar optical detector array and/or a number of scintillation photons in each of a plurality of scintillation light pulses detected by a portion of the planar optical detector array, in response to received gamma quanta; and ii) reconstructing a SPECT image or a gamma scintigraphy image from the gamma decay event data. Advantageously the so-reconstructed images have improved resolution as a result of using the inventive gamma radiation detector.

DETAILED DESCRIPTION OF THE INVENTION

In order to illustrate the principles of the present invention a gamma radiation detector is described with particular reference to the detection of gamma quanta in a SPECT imaging system. It is however to be appreciated that the gamma radiation detector finds application in other medical imaging applications such as the generation of a scintigraphy image, as well as in imaging applications beyond the medical field. Moreover it may be used in non-imaging applications both in and beyond the medical field.

Figure 1:
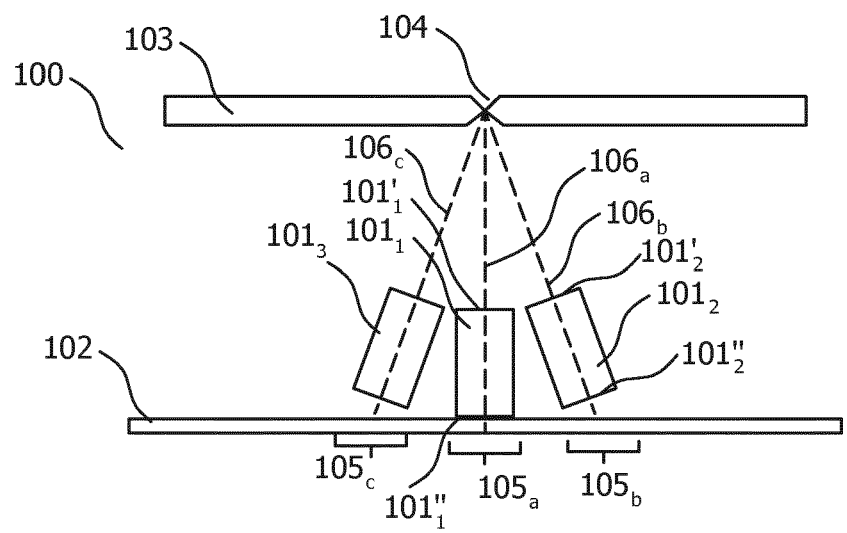
FIG. 1 illustrates a first embodiment of a gamma radiation detector 100 that includes a plurality of scintillator elements $101_{1\ldots n}$, a planar optical detector array 102 and a pinhole collimator 103.

FIG. 1 illustrates a first embodiment of a gamma radiation detector 100 that includes a plurality of scintillator elements $101_{1...n}$, a planar optical detector array 102 and a pinhole collimator 103. Scintillator elements $101_{1...n}$ may each be formed from a wide range of scintillator materials including cesium iodide, e.g. CsI:Tl, cerium doped garnets like yttrium-aluminium garnets, i.e. YAG, gadolinium-aluminium garnets, i.e. GAG, gadolinium-gallium-aluminium garnets, i.e. GGAG, combinations thereof or with other rare earth materials like lutetium or terbium, and also from other scintillator materials. Planar optical detector array 102 converts pulses of scintillation light generated within scintillator elements $101_{1...n}$ into electrical signals. Planar optical detector array 102 may for example include an array of photodetectors such as photodiodes. Preferably an array of silicon photomultiplier, i.e. SiPM, photodiodes is used, such as a Philips Digital Photon Counting, PDPC, SiPM photodetector array. Alternatively planar optical detector array 102 may include an array of photomultiplier tubes, position sensitive photodetectors, and so forth. Pinhole collimator 103 includes at least one pinhole aperture 104. Preferably the pinhole is a circular hole with a diameter in the range 1-5 millimeters. Other shapes of pinhole may alternatively be used such as a slit, a rectangle, a square, or a hexagon. Moreover the thickness of pinhole collimator 103 in a direction perpendicular to its radiation receiving face may be stepped or tapered between a body portion of the collimator and the pinhole aperture 104 and include a knife-edge, a rounded-edge, a chamfered edge or a square edge at the aperture. The body portion may have a thickness in the range 2-20 millimeters. The pinhole may for example have a diameter in the range 1-5 millimeters. Pinhole collimator 103 may be formed from a dense metal such as lead or tungsten or gold. Optionally part of the pinhole collimator surrounding pinhole aperture 104 may be formed from an insert that is formed from a different material to that of the body of the pinhole collimator. Thus for example the body of the collimator may be formed from lead and the insert that includes the pinhole may be formed from tungsten or gold.

Each scintillator element $101_{1...n}$ in FIG. 1 includes gamma radiation receiving face $101'_{1...n}$ and opposing scintillation light output face $101''_{1...n}$. Gamma radiation receiving face $101'_{1...n}$ of each scintillator element is arranged to face pinhole aperture 104 in order to generate scintillation light in response to gamma radiation received from pinhole aperture 104. Moreover the plurality of scintillator elements $101_{1...n}$ are arranged in a plurality of groups $105_{a...z}$. Each group $105_{a...z}$ includes one or more scintillator elements and each group has a group axis $106_{a...z}$ that is aligned with the pinhole aperture and that is perpendicular to the radiation receiving face of each of the one or more scintillators in the each group. Thus a one-to-one coupling, or a one-to-more-than-one coupling between pinhole aperture 104 and scintillator element(s) in each group $105_{a...z}$ may be provided.

Moreover, the scintillation light output face $101''_{1...n}$ of each of the plurality of scintillator elements $101_{1...n}$ in FIG. 1 are in optical communication with planar optical detector array 102. Various forms of such optical communication are contemplated. These include an air path wherein scintillation light generated within each scintillator elements $101_{1...n}$ is projected onto planar optical detector array 102, the use of an optical coupling medium such as optical grease, oil or silicone or optical fibers. Additional light barriers not shown in FIG. 1 may additionally be disposed between neighboring scintillator elements in order to confine the scintillation light generated within each scintillator element to a predetermined portion of planar optical detector array 102.

Advantageously in the arrangement of FIG. 1, since each group axis $106_{a-z}$ is aligned with pinhole aperture 104 it is arranged that gamma quanta absorbed within different groups are absorbed along their respective group axis. This reduces the parallax effect by reducing the gamma quanta acceptance angle of each group, as compared to for example orienting scintillator elements with their group axes parallel to one another. By arranging that the radiation receiving faces of each group are perpendicular to their respective group axis, a more uniform scintillation light distribution pattern is achieved within the scintillator element. Advantageously because the scintillation light output face of each scintillator element is in optical communication with the planar optical detector array a flat optical detector array can be used. This simplifies the manufacturing and assembly of the optical detector array.

Optionally each scintillator element in FIG. 1 includes one or more side faces that extend between its gamma radiation receiving face and its scintillation light output face. Moreover, the gamma radiation receiving face and the one or more side faces of each scintillator element may further include an optical scattering and/or and optical reflecting layer. Such layers may be formed from known materials such as PTFE, Teflon, $TiO_2$, Lumirror®, Enhanced Specular Reflector (ESR) film, Tyvek®, metals include silver and aluminium. Advantageously the above layers improve the retention of scintillation light within the scintillator element within which it is generated.

Figure 2:
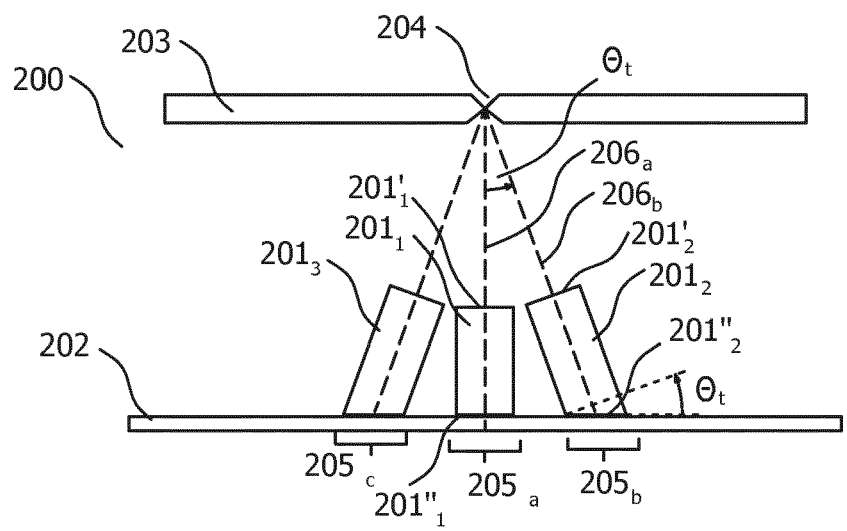
FIG. 2 illustrates a second embodiment of a gamma radiation detector 200 that includes a plurality of scintillator elements $201_{1\ldots n}$, a planar optical detector array 202 and a pinhole collimator 203.

FIG. 2 illustrates a second embodiment of a gamma radiation detector 200 that includes a plurality of scintillator elements $201_{1...n}$, a planar optical detector array 202 and a pinhole collimator 203. The arrangement of FIG. 2 corresponds to that described in relation to FIG. 1 with the additional feature that in FIG. 2 the scintillation light output faces $201''_{1...n}$ of each of the scintillator elements $201_{1...n}$ are parallel to one another.

In more detail, in the gamma radiation detector 200 in the embodiment of FIG. 2, the plurality of groups $205_{a...z}$ includes first group $205_a$ and second group $205_b$. Group axis $206_b$ of second group $205_b$ is tilted at a tilt angle $\theta_t$ with respect to group axis $206_a$ of first group $205_a$. Moreover, scintillation light output face $201''_2$ of each of the one or more scintillator elements in the second group $205_b$ is also tilted at tilt angle $\theta_t$ with respect to its corresponding gamma radiation receiving face $201'_2$ such that the scintillation light output face of each of the one or more scintillator elements in the second group $205_b$ is parallel to the scintillation light output face $201''_1$ of each of the one or more scintillator elements in the first group $205_a$.

By so-shaping the scintillator elements in FIG. 2 the optical coupling efficiency of scintillation light between scintillator elements $201_{1...n}$ and planar optical detector array 202 is improved. Moreover the parallel arrangement of scintillation light output faces $201''_{1...n}$ provides a robust means of coupling the scintillator elements to planar optical detector array 202. Scintillator elements $201_{1...n}$ may for example be attached to planar optical detector array 202 by an optically-transparent adhesive or by means of a mechanical mount configured to receive scintillator elements $201_{1...n}$ and which is not shown in FIG. 2.

Figure 3:
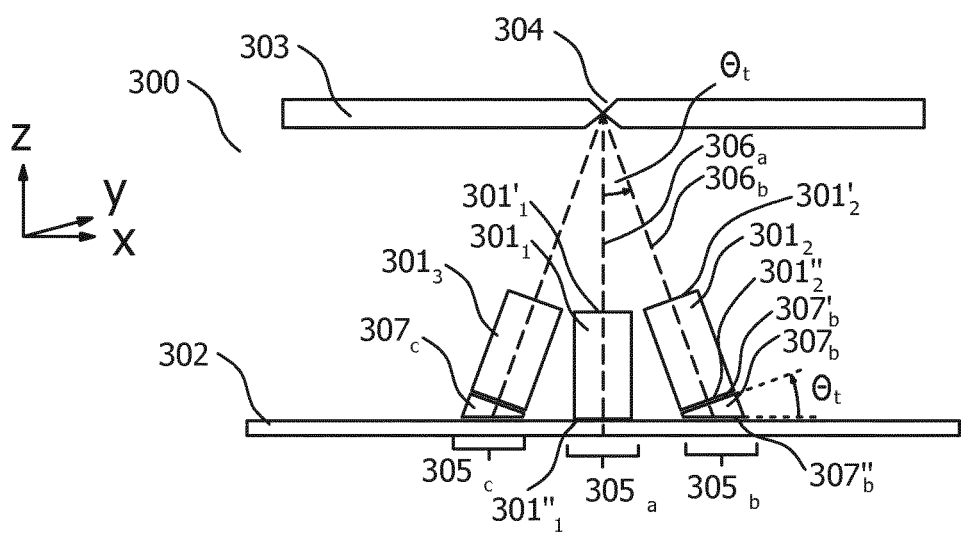
FIG. 3 illustrates a third embodiment of a gamma radiation detector 300 that includes a plurality of scintillator elements $301_{1\ldots n}$, a planar optical detector array 302 and a pinhole collimator 303.

Optionally gamma radiation detector 200 illustrated in FIG. 2, or correspondingly that in FIG. 1 or FIG. 3, may further include a crystal efficiency normalization unit that is in communication with planar optical detector array 202.

The crystal efficiency normalization unit may for example be a processor. The crystal efficiency normalization unit is configured to receive data from a plurality of discrete portions of the planar optical detector array, wherein each discrete portion is in optical communication with a separate scintillator element, and wherein the data corresponds to the number of scintillation photons in a light pulse generated by a scintillator element in response to a received gamma quant. Moreover, the crystal efficiency normalization unit is configured to apply a scintillator element normalization factor to the data received from each discrete portion of the planar optical detector array. The scintillator element normalization factor is based on the distance between the radiation receiving face and the scintillation light output face of the corresponding scintillator element. In use the different sizes, or more specifically the different lengths of scintillator elements in the configuration of FIG. 2 may result in different numbers of detected scintillation photons for each detected gamma quant. This can for example be caused by optical attenuation of the scintillation photons within the scintillator. Since the number of detected scintillation photons is indicative of the number of detected gamma quanta, errors in the former can give rise to errors in the activity of a gamma source. The length-dependent correction factor applied by the normalization unit can thus be used to reduce these errors.

FIG. 3 illustrates a third embodiment of a gamma radiation detector 300 that includes a plurality of scintillator elements $301_{1\ldots n}$, a planar optical detector array 302 and a pinhole collimator 303. The arrangement of FIG. 3 corresponds to that described in relation to FIG. 1 with the additional feature that the embodiment of FIG. 3 further includes one or more wedge-shaped light guides $307_b$ disposed between each scintillator element $301_2$ of the second group $305_b$ and the planar optical detector array 302.

In more detail, in the gamma radiation detector 300 in the embodiment of FIG. 3, the plurality of groups $305_{a\ldots z}$ includes first group $305_a$ and second group $305_b$. Group axis $306_b$ of the second group $305_b$ is tilted at tilt angle $\theta_t$ with respect to the group axis $306_a$ of first group $305_a$. The scintillation light output face $301''_2$ of each of the one or more scintillator elements in the second group $305_b$ is parallel to its corresponding gamma radiation receiving face $301'_2$. Moreover, second group $305_b$ includes one or more wedge-shaped light guides $307_b$ disposed between each scintillator element $301_2$ of the second group $305_b$ and the planar optical detector array 302. Each wedge-shaped light guide $307_b$ has a first face $307'_b$ and a second face $307''_b$, the second face $307''_b$ being arranged at tilt angle $\theta_t$ to the corresponding first face $307'_b$ for coupling scintillation light between the scintillation light output face $301''_2$ of the corresponding scintillator element $301_2$ and planar optical detector array 302 via the first face $307'_b$ and the second face $307''_b$.

Advantageously in FIG. 3 the parallel arrangement of each scintillator element's gamma radiation receiving face with respect to its scintillation light output face in combination with the wedge shaped light guide provides high light coupling efficiency with the array. Moreover it permits the use of simpler manufacturing methods in making the scintillator elements. Such scintillator shapes are more robust to handling during assembly.

Figure 5:
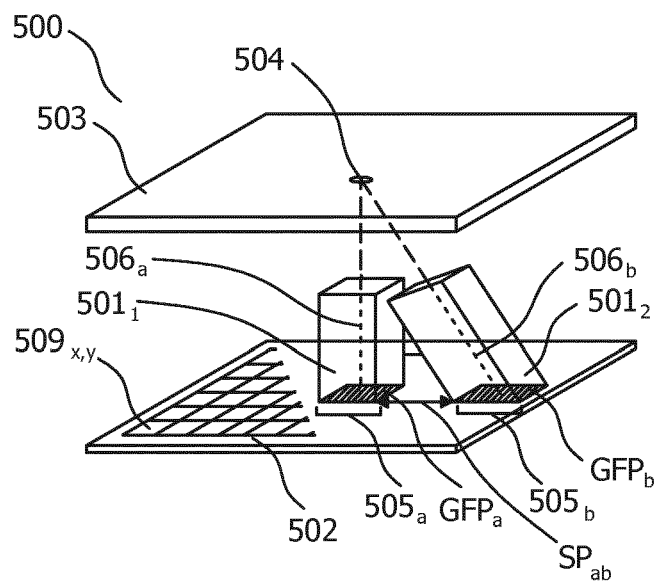
FIG. 5 illustrates a gamma radiation detector 500 in which the planar optical detector array 502 includes only one continuous array of regularly-spaced optical detector elements $509_{x,y}$, and in which the scintillation light output faces of each group of scintillator elements $505_a$, $505_b$ define a group footprint $GFP_a$, $GFP_b$.

Optionally each scintillator element in the first group $305_a$ and the second group $305_b$ in FIG. 5 has a length between the center of its gamma radiation receiving face ($301'_1$, $301'_2$) and the center of its scintillation light output face ($301''_1$, $301''_2$). Moreover the length of each scintillator element in the first group $305_a$ is optionally equal to the length of each scintillator element in the second group $305_b$. Advantageously by making the lengths equal the manufacturing of the gamma radiation detector is simplified because a common size of scintillator elements may be used.

Figure 4:
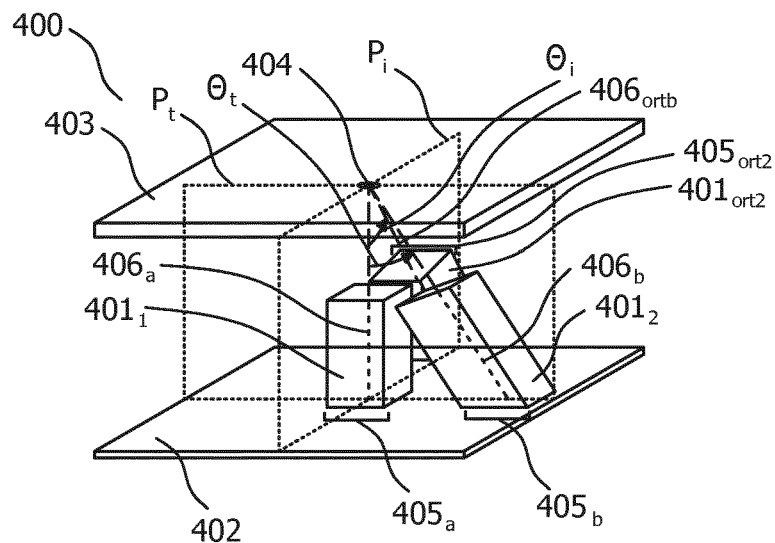
FIG. 4 illustrates a fourth embodiment of a gamma radiation detector 400 that includes an orthogonal group $405_{ort2}$ of one or more scintillator elements $401_{ort2}$.

FIG. 4 illustrates a fourth embodiment of a gamma radiation detector 400 that includes an orthogonal group $405_{ort2}$ of one or more scintillator elements $401_{ort2}$. The groups of scintillator elements in the invention may thus be arranged in a two-dimensional array of groups wherein each group has a group axis that is aligned with the pinhole aperture 404 of pinhole collimator 403. In more detail gamma radiation detector illustrated in FIG. 4 includes an orthogonal group $405_{ort2}$ of one or more scintillator elements $401_{ort2}$. The group axis $406_{ortb}$ of the orthogonal group $405_{0,12}$ is inclined at an inclined angle $\theta$, with respect to the group axis $406_a$ of the first group $405_a$. Moreover the group axis $406_{ortb}$ is inclined in a plane $P_i$ that is orthogonal with respect to a plane $P_t$ that includes the tilt of the tilt angle $\theta_t$ of the second group $405_b$. Advantageously the field of view of gamma radiation detector 400 is improved by providing the orthogonal group. Although only three scintillator element groups are illustrated in FIG. 4, additional groups that form a complete e.g. 2×2, 4×4 and so forth, rectangular, hexagonal, circular and so forth, 2D-array of scintillator elements may also be used. Moreover, whilst the scintillator element geometry of FIG. 4 is illustrated as being that of FIG. 2; i.e. with the scintillation light output face of the second and orthogonal groups tilted with respect to its corresponding radiation receiving face, it is also to be appreciated that the gamma radiation detector of FIG. 4 may also be used with the scintillator element geometry of FIG. 1 or FIG. 3 with corresponding benefits.

FIG. 5 illustrates a gamma radiation detector 500 in which the planar optical detector array 502 includes only one continuous array of regularly-spaced optical detector elements $509_{x,y}$, and in which the scintillation light output faces of each group of scintillator elements $505_a$, $505_b$ define a group footprint $GFP_a$, $GFP_b$. The optical detector elements in the planar optical detector array 502, e.g. photodetector or photodiodes, thus have a fixed pitch in for example in one direction in the case of a linear array or for example in orthogonal directions in the case of a 2D array. Moreover each group footprint $GFP_a$, $GFP_b$ in FIG. 5 is laterally separated from its one or more neighboring group footprints $GFP_a$, $GFP_b$ by a corresponding space $SP_{ab}$. The one or more spaces $SP_{ab}$ each define a region of the only one continuous array having optical detector elements that are not in optical communication with a scintillator element $501_1$, $501_2$. The one or more spaces $SP_{ab}$ may for example be 1, 2, 5, or 10 or more pixels wide. Thus there are unused portions of the optical detector array. Advantageously the use of a single array of photodetector elements in gamma radiation detector 500 alleviates the need to design an array that exactly matches each group footprint, thereby simplifying manufacturing. Optionally the unused portions of the optical detector array may be ignored, i.e. not read-out during the detection of scintillation light, thereby reducing readout time.

Figure 6:
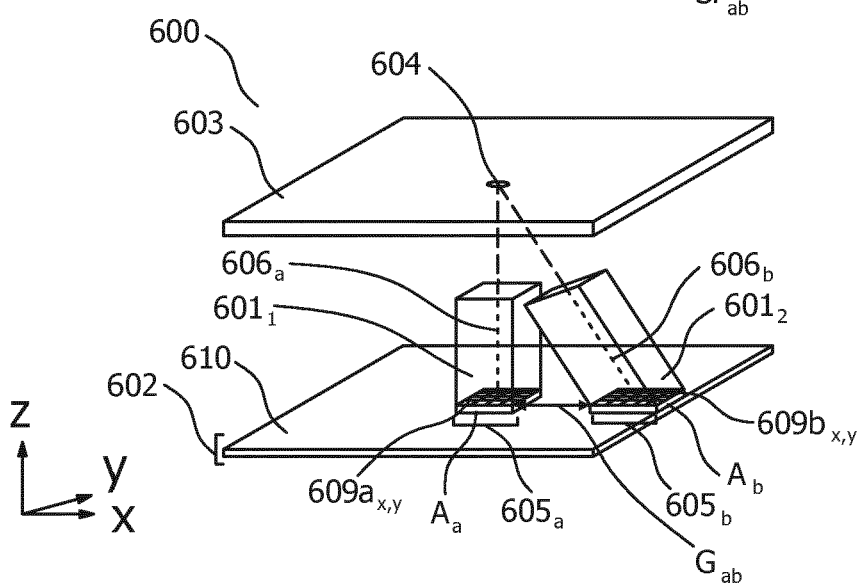
FIG. 6 illustrates a gamma radiation detector 600 in which the planar optical detector array 602 comprises a plurality of continuous arrays $A_a$, $A_b$ of regularly-spaced optical detector elements $609a_{x,y}$, $609b_{x,y}$, each continuous array being disposed on a common planar surface 610.

FIG. 6 illustrates a gamma radiation detector 600 in which the planar optical detector array 602 comprises a plurality of continuous arrays $A_a$, $A_b$ of regularly-spaced optical detector elements $609a_{x,y}$, $609b_{x,y}$, each continuous array being disposed on a common planar surface 610. In FIG. 6, each continuous array is thus a separate or discrete array of optical detector elements. Moreover, each continuous array $A_a$, $A_b$ in FIG. 6 is laterally separated from its one or more neighboring arrays $A_a$, $A_b$ by a corresponding gap $G_{ab}$. In the gap there are thus no photodetector elements, or at least there is a reduced area density of photodetector elements as compared to that in each continuous array. Moreover, each group of the plurality of scintillator element groups $605_a$, $605_b$ is optically coupled to a different continuous array $A_a$, $A_b$. In so doing the gamma radiation detector 600 saves photodetector area. Such a sparse array can therefore be made at low cost.

Figure 7:
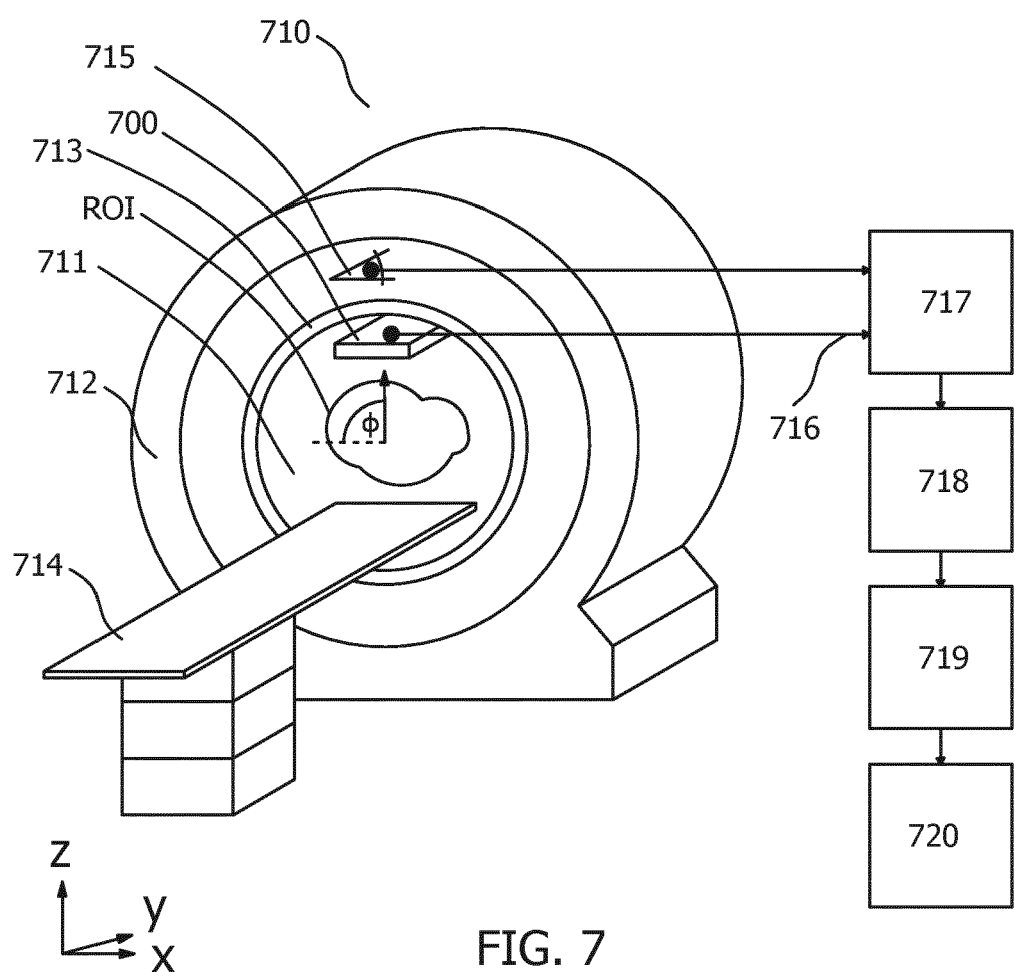
FIG. 7 illustrates a SPECT imaging system 710 that includes at least one gamma radiation detector 700.

FIG. 7 illustrates a SPECT imaging system 710 that includes at least one gamma radiation detector 700. SPECT imaging system 710 may be used to image a region of interest ROI within examination region 711 in order to determine a distribution of a radiotracer therein. SPECT imaging system 710 includes fixed gantry 712 that supports rotatable gantry 713 to which one or more gamma radiation detectors 700 are mounted. Support pallet 714 may be used to convey an object that includes region of interest ROI into examination region 711 in order to perform such an imaging procedure. Gamma radiation detector 700 may be any of the embodiments of a gamma radiation detector described above. Preferably, multiple such gamma radiation detectors are used, these being disposed either i) on a common plane as illustrated, or ii) radially about the examination region 711, such that their pinholes are each directed at, i.e. focused on, a portion of region of interest ROI. In operation, SPECT imaging system 710 may be operated in the following manner Gamma radiation detector(s) 700 are oriented towards region of interest ROI in order to detect gamma quanta that are emitted by a radiotracer therein during the radiotracer's decay. The position of gamma radiation detector(s) 700 respective examination region 711 may be detected by optional detector position unit 715. Detector position unit may for example include an angular sensor configured to determine the rotational positon $\phi$ of a portion of rotatable gantry 713 respective fixed gantry 712. The planar optical detector array(s), not shown in FIG. 7, of gamma radiation detector(s) 700 generate electrical signals, i.e. gamma decay event data 716 corresponding to the detected gamma quanta. Gamma decay event data 716 are indicative of one or more of i) the number of decay events, ii) the number of scintillation light photons generated in response to a detected decay event iii) the identity of each optical detector element in each gamma radiation detector(s) 700 corresponding to the decay event data, iv) the time at which each decay event is detected. Data memory 717 receives and stores gamma decay event data 716 and provides this data to reconstruction processor 718. Reconstruction processor 718 reconstructs this data, optionally including position data generated by detector position unit 715, into one or more tomographic images corresponding to the distribution of radiotracer within region of interest ROI using known image reconstruction methods. Video processor 719 subsequently formats the reconstructed image data for display on display device 720.

In another configuration the SPECT imaging system of FIG. 7 may be operated with the rotatable gantry in a static position during which data corresponding to a radiotracer distribution within region of interest ROI is acquired in a manner similar to that described above. In this configuration the reconstruction processor generates an image of the radiotracer distribution with the rotatable gantry in a static position, i.e. a scintigraphy image.

In another configuration, not illustrated, a scintigraphy image may be generated by a gamma imaging camera. The gamma imaging camera may include one or more gamma radiation detectors as described herein, in combination with a reconstruction processor. As in the SPECT imaging system 710 described above, the gamma imaging camera may be arranged adjacent to a region of interest in order to detect gamma quanta that are emitted by a radiotracer therein during the radiotracer's decay. The planar optical detector array(s) of the gamma radiation detector(s) generate electrical signals, i.e. gamma decay event data corresponding to the detected gamma quanta. The gamma decay event data are indicative of one or more of i) the number of decay events, ii) the number of scintillation light photons generated in response to a detected decay event iii) the identity of each optical detector element in each gamma radiation detector(s) 700 corresponding to the decay event data, iv) the time at which each decay event is detected. A data memory then receives and stores gamma event data and provides this data to a reconstruction processor that reconstructs the data into one or scintigraphy images corresponding to the distribution of radiotracer within the region of interest using known reconstruction methods.

SPECT imaging system 710 in FIG. 7 may also include a system processor that is not shown in FIG. 7. The system processor may be in communication with at least data memory 717 and reconstruction processor 718. Moreover one or both of reconstruction processor 718 and video processor 719 may also be included within the system processor. The system processor may be configured to control SPECT imaging system 710. The system processor may include computer-readable instructions which when executed on the system processor cause the processor to carry-out the method steps of: i) receiving, from the planar optical detector array of the gamma radiation detector of claim 1, gamma decay event data 716 corresponding to a number of scintillation light pulses detected by a portion of the planar optical detector array and/or a number of scintillation photons in each of a plurality of scintillation light pulses detected by a portion of the planar optical detector array, in response to received gamma quanta; and ii) reconstructing a SPECT image or a gamma scintigraphy image from the gamma decay event data 716. Moreover the above method steps, and/or other method steps disclosed herein, may be recorded in the form of instructions on computer-readable medium that is executable by a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In summary, a gamma radiation detector 100, 200, 300, 400, 500, 600, 700 that provides compensation for the parallax effect has been described. The gamma radiation detector includes a plurality of scintillator elements $101_{1...n}, 201_{1...n}, 301_{1...n}$, a planar optical detector array 102, 202, 302, and a pinhole collimator 103, 203, 303 that includes a pinhole aperture 104, 204, 304. Each scintillator element has a gamma radiation receiving face $101'_{1...n}$, $201'_{1...n}, 301'_{1...n}$ and an opposing scintillation light output face $101''_{1...n}, 201''_{1...n}, 301''_{1...n}$. The gamma radiation receiving face of each scintillator element faces the pinhole aperture for generating scintillation light in response to gamma radiation received from the pinhole aperture. The scintillator elements are arranged in groups $105_{a...z}$, $205_{a...z}, 305_{a...z}$. Each group has a group axis $106_{a...z}, 206_{a...z}, 306_{a...z}$ that is aligned with the pinhole aperture and is perpendicular to the radiation receiving face of each scintillator in that group. The scintillation light output faces of each of the scintillator elements are in optical communication with the planar optical detector array.

The invention claimed is:

1. A gamma radiation detector comprising:
a plurality of scintillator elements, each of the plurality of scintillator elements comprising a gamma radiation receiving face and an opposing scintillation light output face, the plurality of scintillator elements being arranged in a plurality of groups comprising a first group and a second group, wherein: a group axis of the second group is tilted at a tilt angle with respect to a group axis of the first group; and the opposing scintillation light output face of each of the plurality of scintillator elements in the second group is also tilted at the tilt angle with respect to its corresponding gamma radiation receiving face such that the opposing scintillation light output face of each of the plurality of scintillator elements in the second group is parallel to the opposing scintillation light output face of each of the plurality of scintillator elements in the first group;
a planar optical detector array, the opposing scintillation light output face of each of the plurality of scintillator elements being in optical communication with the planar optical detector array; and
a pinhole collimator comprising a pinhole aperture, the gamma radiation receiving face of each scintillator element being arranged to face the pinhole aperture for generating scintillation light is response to gamma radiation received from the pinhole aperture, each of the plurality of groups comprising one or more scintillator elements and each group having a group axis that is aligned with the pinhole aperture and that is perpendicular to the gamma radiation receiving face of each of the one or more scintillators in each of the plurality of groups, wherein the opposing scintillation light output face of each of the plurality of scintillator elements is in optical communication with the planar optical detector array.

2. The gamma radiation detector according to claim 1, further comprising;
a processor; and
receive data from a plurality of discrete portions of the planar optical detector array, wherein each discrete portion is in optical communication with a separate scintillator element, and wherein the data corresponds to a number of scintillation photons in alight pulse generated by a scintillator element in response to a received gamma quant; and
apply a scintillator element normalization factor to the data received from each discrete portion of the planar optical detector array, and wherein the scintillator element normalization factor is based on a distance between the radiation receiving face and the opposing scintillation light output face of a corresponding scintillator element.

3. The gamma radiation detector according to claim 1, wherein; the plurality of groups comprises an orthogonal group comprising one or more scintillator elements; a group axis of the orthogonal group is inclined at an inclined angle with respect to the group axis of the first group; and the group axis of the orthogonal group is inclined in a plane that is orthogonal with respect to a plane that comprises a tilt of the tilt angle of the second group.

4. The gamma radiation detector according to claim 1, wherein:
each scintillator element further comprises one or more side faces that extend between its gamma radiation receiving face and its scintillation light output face; and
the gamma radiation receiving face and the one or more side faces of each scintillator element further comprise an optical scattering and/or and optical reflecting layer.

5. The gamma radiation detector according to claim 1, wherein:
the planar optical detector array comprises only one continuous array of regularly-spaced optical detector elements; and wherein the opposing scintillation light output face of each group define a group footprint; and wherein each group footprint is laterally separated from its one or more neighboring group footprints by a corresponding space; and
the one or more spaces each define a region of the only one continuous array having optical detector elements that are not in optical communication with a scintillator element.

6. The gamma radiation detector according to claim 1 wherein:
the planar optical detector array comprises a plurality of continuous arrays of regularly-spaced optical detector elements, each continuous array being disposed on a common planar surface;
each continuous array is laterally separated from its one or more neighboring arrays a corresponding gap; and
each group of the plurality of groups is optically coupled to a different continuous array.

7. A SPECT imaging system comprising at least one gamma radiation detector according to claim 1.

8. A gamma imaging camera for generating a gamma scintigraphy image, the gamma imaging camera comprising the gamma radiation detector according to claim 1.

9. A method of image reconstruction, the method comprising:
receiving, from the planar optical detector array of the gamma radiation detector of claim 1, gamma decay event data corresponding to a number of scintillation light pulses detected by a portion of the planar optical detector array and/or a number of scintillation photons in each of a plurality of scintillation light pulses detected by a portion of the planar optical detector array, in response to received gamma quanta, reconstructing a SPECT image or a gamma scintigraphy image from the gamma decay event data.

10. A tangible, non-transitory computer readable medium that stores instructions, which when executed by a processor, cause the processor to carry out the method according to claim 9.

11. A gamma imaging camera for generating a gamma scintigraphy image, the gamma imaging camera comprising the gamma radiation detector according to claim 1.

12. A gamma radiation detector comprising:
   a plurality of scintillator elements, the plurality of scintillator elements being arranged in a plurality of groups, each of the plurality of scintillator elements comprising a gamma radiation receiving face and an opposing scintillation light output face;
   a planar optical detector array, the opposing scintillation light output face of each of the plurality of scintillator elements being in optical communication with the planar optical detector array; and
   a pinhole collimator comprising a pinhole aperture, the gamma radiation receiving face of each scintillator element being arranged to face the pinhole aperture for generating scintillator light in response to gamma radiation received from the pinhole aperture, each of the plurality of groups comprising one or more scintillator elements and each group having a group axis that is aligned with the pinhole aperture and that is perpendicular to the gamma radiation receiving face of each of the one or more scintillator in each of the plurality of groups, wherein the opposing scintillation light output face of each of the plurality of scintillator elements is in optical communication with the planar optical detector array;
   a processor; and
   a memory that stores instructions, which when executed by the processor cause the processor to: receive data from a plurality of discrete portions of the planar optical detector array, wherein each discrete portion is in optical communication with a separate scintillator element, and wherein the data corresponds to a number of scintillation photons in a light pulse generated by a scintillator element in response to a received gamma quant; and apply a scintillator element normalization factor to the data received from each discrete portion of the planar optical detector array, and wherein the scintillator element normalization factor is based on a distance between the radiation receiving face and the opposing scintillation light output face of a corresponding scintillator element.

13. The gamma radiation detector according to claim 12, wherein:
   the plurality of groups includes a first group and a second group;
   a group axis of the second group is tilted at a tilt angle with respect to a group axis of the first group;
   the opposing scintillation light output face of each of multiple scintillator elements in the second group is parallel to its corresponding gamma radiation receiving face; and
   the second group comprises one or more wedge-shaped light guides disposed between each scintillator element of the second group and the planar optical detector array, each wedge-shaped light guide having a first face and a second face, the second face being arranged at the tilt angle to a corresponding first face for coupling scintillation light between the opposing scintillation light output face of the corresponding scintillator element and the planar optical detector array via the first face and the second face.

14. The gamma radiation detector according to claim 13, wherein: each scintillator element in the first group and the second group has a length between the center of its gamma radiation receiving face and the center of its scintillation light output face; and the length of each scintillator element in the first group is equal to the length of each scintillator element in the second group.

15. The gamma radiation detector according to claim 13, wherein:
   the plurality of groups comprises an orthogonal group comprising one or more scintillator elements; and
   a group axis of the orthogonal group is inclined at an inclined angle with respect to the group axis of the first group, the orthogonal group axis being inclined in a plane that is orthogonal with respect to a plane that comprises a tilt of the tilt angle of the second group.

16. The gamma radiation detector according to claim 12, wherein:
   each scintillator element further comprises one or more side faces that extend between its gamma radiation receiving face and its scintillation light output face; and
   the gamma radiation receiving face and the one or more side faces of each scintillator element further comprise an optical scattering and/or and optical reflecting layer.

17. The gamma radiation detector according to claim 12, wherein:
   the planar optical detector array comprises only one continuous array of regularly-spaced optical detector elements; and
   the opposing scintillation light output faces of each group define a group footprint; and wherein each group footprint is laterally separated from its one or more neighboring group footprints by a corresponding space; and wherein the one or more spaces each define a region of the only one continuous array having optical detector elements that are not in optical communication with a scintillator element.

18. The gamma radiation detector according to claim 12, wherein:
   planar optical detector array comprises a plurality of continuous arrays of regularly-spaced optical detector elements, each continuous array being disposed on a common planar surface; and
   each continuous array is laterally separated from its one or more neighboring arrays a corresponding gap; and wherein each group of the plurality of scintillator element groups is optically coupled to a different continuous array.

19. A SPECT imaging system comprising at least one gamma radiation detector according to claim 12.

20. A gamma radiation detector comprising:
   a plurality of scintillator elements arranged in a plurality of groups, each of the plurality of groups comprising multiple scintillator elements, wherein each scintillator element comprises a gamma radiation receiving face and an opposing scintillation light output face;
   a planar optical detector array, the opposing scintillation light output face of each of the plurality of scintillator elements being in optical communication with the planar optical detector array; and
   a pinhole collimator comprising a pinhole aperture, the gamma radiation receiving face of each scintillator element being arranged to face the pinhole aperture for generating scintillation light in response to gamma radiation received from the pinhole aperture, each of the plurality of groups comprising multiple scintillator elements and each group having a group axis that is aligned with the pinhole aperture and that is perpendicular to the gamma radiation receiving face of each of the multiple scintillator elements in each of the plurality of groups, wherein the opposing scintillation light output face of each of the plurality of scintillator elements is in optical communication with the planar optical detector array.

21. The gamma radiation detector according to claim 20, wherein:

the planar optical detector array comprises only one continuous array of regularly-spaced optical detector elements; and wherein the opposing scintillation light output faces of each group define a group footprint; and wherein each group footprint is laterally separated from its one or more neighboring group footprints by a corresponding space; and the one or more spaces each define a region of the only one continuous array having optical detector elements that are not in optical communication with a scintillator element.

22. The gamma radiation detector according to claim 20, wherein:

the planar optical detector array comprises a plurality of continuous arrays of regularly-spaced optical detector elements, each continuous array being disposed on a common planar surface;

each continuous array is laterally separated from its one or more neighboring arrays a corresponding gap; and each group of the plurality of groups is optically coupled to a different continuous array.

* * * * *